(12) United States Patent
Noguchi

(10) Patent No.: US 6,456,318 B1
(45) Date of Patent: Sep. 24, 2002

(54) DEFECT INSPECTION APPARATUS AND METHOD BY COMPARING TWO PAIRS OF AREAS ADJACENT TO ONE ANOTHER

(75) Inventor: Syun Noguchi, Mitaka (JP)

(73) Assignee: Tokyo Seimitsu Co., Ltd., Tokyo (JP)

( * ) Notice: Subject to any disclaimer, the term of this patent is extended or adjusted under 35 U.S.C. 154(b) by 0 days.

(21) Appl. No.: 09/294,147

(22) Filed: Apr. 20, 1999

(30) Foreign Application Priority Data

Apr. 24, 1998 (JP) ............................................ 10-114782

(51) Int. Cl.[7] ................................................. H04N 7/18
(52) U.S. Cl. ............................ 348/87; 348/92; 348/126; 348/130
(58) Field of Search .............................. 348/87, 88, 92, 348/94, 95, 126, 129, 130; 382/141, 144, 145, 147, 149, 151, 227; 356/390, 394; H04N 7/18

(56) References Cited

U.S. PATENT DOCUMENTS 4,791,586 A  * 12/1988  Maeda et al. ............... 382/149
5,153,444 A     10/1992  Maeda et al.
5,295,198 A  *  3/1994  Maney ........................ 382/227

FOREIGN PATENT DOCUMENTS

| DE | 197 34 486 A | 2/1998 |
|---|---|---|
| EP | 0 374 694 | 6/1990 |
| JP | 61038450 | 2/1986 |
| JP | A-2-210249 | 8/1990 |
| JP | 10054806 A | 2/1998 |
| TW | 350111 | 1/1999 |
| WO | WO 96/39619 | 12/1996 |

* cited by examiner

Primary Examiner—Young Lee
(74) Attorney, Agent, or Firm—Oliff & Berridge PLC

(57) ABSTRACT

A Time Delayed Integrator (TDI) sensor obtains images of a plurality of areas with the same pattern of an object of inspection such as a semiconductor wafer, and the obtained images are stored in an image storage part. The plurality of areas are designated in airs, and an image comparison part compares the images of the areas in each pair to detect a suspected pair including at least one possible defective area. A central processing unit (CPU) compares the images of the areas in the suspected pair with images of areas in other pairs to thereby find which area in the suspected pair is defective.

8 Claims, 6 Drawing Sheets

F I G. 2
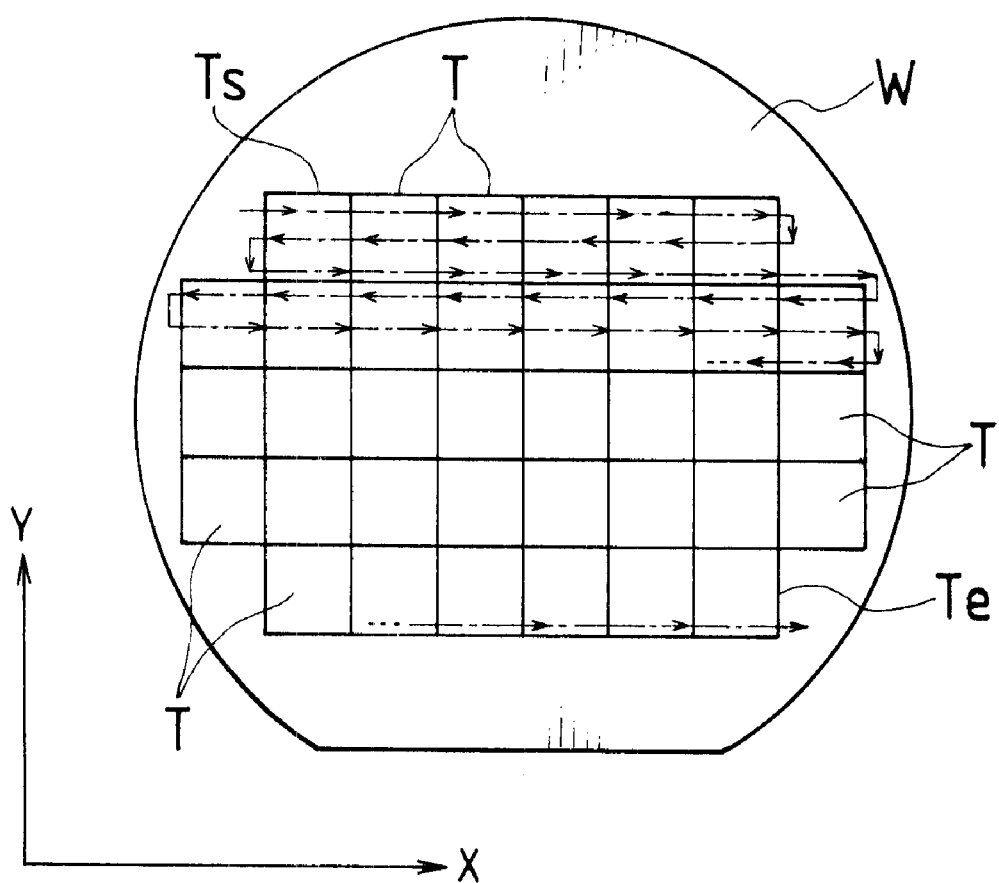

DEFECT INSPECTION APPARATUS AND METHOD BY COMPARING TWO PAIRS OF AREAS ADJACENT TO ONE ANOTHER

BACKGROUND OF THE INVENTION

1. Field of the Invention

The present invention relates generally to a visual inspection apparatus and method, and more particularly to a visual inspection apparatus and method applied to find defects in patterns on a semiconductor wafer, a photo mask, a liquid crystal display, or the like.

2. Description of Related Art

Conventionally, two adjacent chips are compared to each other in order to inspect patterns on a semiconductor wafer, a photo mask, a liquid crystal display, or the like. In order to inspect the patterns, an image obtaining part, which is composed of an optical microscope and an imaging device such as a time delay and integration (TDI) sensor, obtains images of the patterns represented with multiple values while continuously scanning the object along the x-axis. The obtained images are stored in an image data storage part such as a memory. When two images in the corresponding areas on the adjacent first and second chips are obtained, sub-pixel alignment is performed for these two images at regular frame intervals, and the two images are compared with each other on a pixel-by-pixel basis. In this comparison, a pair of a pixel of the first image and the corresponding pixel of the second image that has a gray level difference in excess of a preset threshold is recognized as having a possibility of being defective. At this point in such single detection, it is not clear which chip of the first and second chips has a possibility of being defective, and thus, a differential image of the first and second images is temporarily stored in a defect detecting part as two values. The above-mentioned comparison is performed between the second chip and the third chip to obtain another differential image, which is collated with the differential image of the first and second chips. It is therefore possible to determine which chip of the first and second chips has a possibility of being defective. In this detecting method (double detection), it is possible to determine defective parts on the chips and improve the reliability of the results since the same chip is subjected to the comparison twice.

In the conventional method, however, each chip is compared with two adjacent chips regardless of whether the chip has a possibility of being defective or not. Therefore, an image comparison part must have the adequate capacity for this purpose, which requires a higher cost.

Only the single detection is performed for edge chips. Thus, the unreliable inspection must be allowed, only the edge chips are not determined, or, only the area that is determined as having a possibility of being defective as a result of the single detection is scanned again after the inspection with respect to the entire surface of the wafer, and the edge chip is compared with the second chip from the edge chip to thereby determine whether the edge chip has a possibility of being defective.

Alternatively, in a scanning method of Japanese Patent Provisional Publication No. 2-210249, the last chip in each scanning line is compared with the first chip in the next scanning line in the double detection. Since, however, the straightness in the scanning direction along the x-axis is higher than the absolute position accuracy along the y-axis, the difference of the images along the y-axis is greater than that of the images of chips in the same scanning lines. Consequently, the images are badly deteriorated by the sub-pixel alignment during the comparison of the images.

SUMMARY OF THE INVENTION

In view of the foregoing, it is an object of the present invention to provide a visual inspection apparatus, which is capable of detecting defects accurately, reducing processing and increasing processing speed.

To achieve the above-mentioned object, the present invention is directed to a visual inspection apparatus, comprising: an imaging means for obtaining images of a plurality of areas on an object; a first image comparison means for designating the plurality of areas in pairs and comparing the images of the areas in each of the pairs to determine whether said each of the pairs is a defective pair including a defective area containing a defective part; and a second image comparison means for comparing the image of one of the areas in the pair determined as the defective pair by the first image comparison means with the image of one of the areas in another of the pairs to determine whether the one of the areas in the pair determined as the defective pair is the defective area.

The first image comparison means may designate the plurality of areas in the pairs of two areas adjacent to one another.

The second image comparison means may compare the image of the one of the areas in the pair determined as the defective pair with the image of one of the areas in another of the pairs adjacent to the one of the areas in the pair determined as the defective pair.

The second image comparison means may compare only a suspected part, including a possible defective part determined by the first image comparison means, of the image of the one of the areas in the pair determined as the defective pair with a part, corresponding to the suspected part, of the image of the one of the areas in said another of the pairs.

According to the present invention, the images of all areas on the object are not always compared twice. The areas are paired, and two images are compared in each pair. Only an image in the pair, which is possibly defective is compared with an image in another pair. This reduces the number of comparisons to almost fifty percent of that of the prior art and increases the processing speed while maintaining the reliability of the conventional double detection.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein:

FIG. 2 is a view showing an example of a scanning track of a TDI sensor on a wafer;

DETAILED DESCRIPTION OF THE PREFERRED EMBODIMENT

This invention will be described in further detail by way of example with reference to the accompanying drawings.

Figure 1:
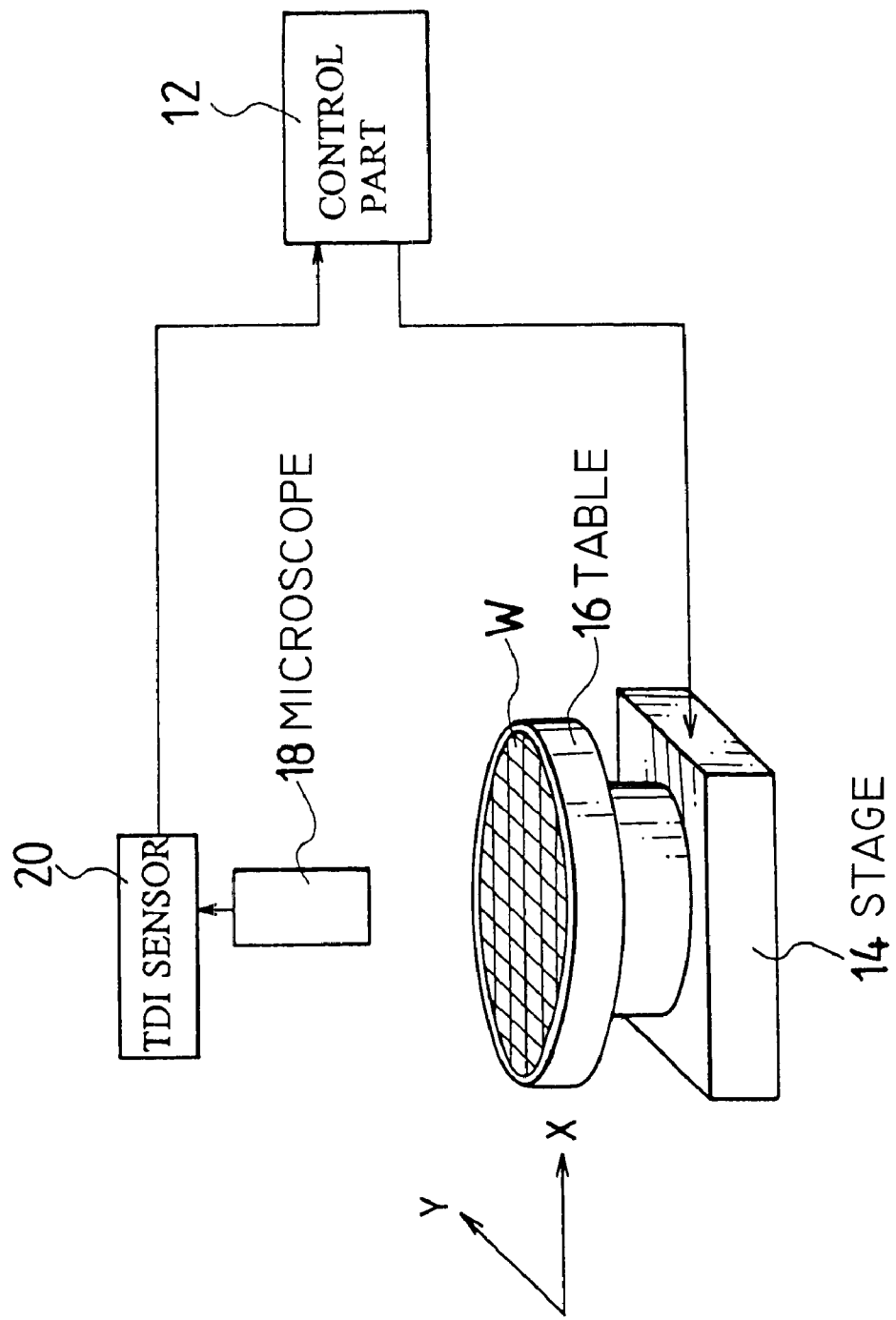
FIG. 1 is a view showing the entire structure of an embodiment of a visual inspection apparatus according to the present invention.

FIG. 1 is a view showing the entire structure of a preferred embodiment of a visual inspection apparatus, which determines whether each chip on a wafer contains a defective part or not. As shown in FIG. 1, the visual inspection apparatus comprises: a control part 12, which performs a variety of processing; an XY stage 14, which moves along X and Y axes horizontally under the control of the control part 12; a sample table 16 provided on the XY stage 14; a microscope 18 arranged above the sample table 16; and a TDI sensor 20 attached at the focusing position of the microscope 18.

A wafer W as an object is placed on the sample table 16. An image of the surface of the wafer W is enlarged and formed on an imaging surface of the TDI sensor 20 by the microscope 18.

As is well known, the TDI sensor 20 is a multistage sensor composed of one-dimensional line sensors such as charge-coupled device (CCD) line sensors. Signal electric charges accumulated in CCD elements of the line sensor at each stage are sequentially transferred to CCD elements of the line sensor at the next stage in synchronism with a scanning speed. Consequently, a plurality of CCD elements overlaps the signal electric charges at one point subject for imaging. Therefore, even if the electric charges are accumulated in each CCD element only for a short period, the signal electric charges at each point subject for imaging are amplified to make up for the shortage in the quantity of light. Thus, the TDI sensor 20 is able to scan the images at a higher speed than the ordinary single-stage CCD line sensor.

In the visual inspection apparatus of the embodiment, the TDI sensor 20 scans the surface of the wafer W along the X-axis. The TDI sensor 20 scans the surface image of the wafer W, which is moved by the XY stage 14 along the X-axis. In this embodiment, the TDI sensor 20 is used as the imaging means, but it is possible to use the ordinary one-dimensional sensor such as the CCD line sensor or a two-dimensional sensor.

The control part 12 controls the XY stage 14 to move the wafer W along the X and Y-axes. The control part 12 controls the TDI sensor 20, which relatively scans the wafer W, and obtains the surface image of the wafer W from the TDI sensor 20. FIG. 2 shows an example of a scanning track of the TDI sensor 20 on the wafer W under the control of the control part 12. As shown in FIG. 2, a number of chips T are regularly arranged along the X and Y-axes on the wafer W, and the chips have the same patterns. As indicated by a dashed and dotted line in FIG. 2, the TDI sensor 20 starts scanning the wafer W along the X-axis from the upper left corner of a chip $T_s$ on the highest line, and reciprocally scans the wafer W until it reaches a chip $T_e$ on the lowest line. The TDI sensor 20 shifts the scanning line along the Y-axis downward little by little (by the image reading width (scanning width) in a direction along the Y-axis perpendicular to the scanning direction along the X-axis) to complete the scanning for all the chips T arranged on the wafer W. The scanning is not necessarily performed on the scanning track in FIG. 2, but the scanning may also be performed in any other scanning tracks.

Then, the control part 12 sends the obtained surface image of the wafer W to a defect detecting part, which is a component of the control part 12. The defect detecting part detects a defective part in each chip on the wafer W.

Figure 3:
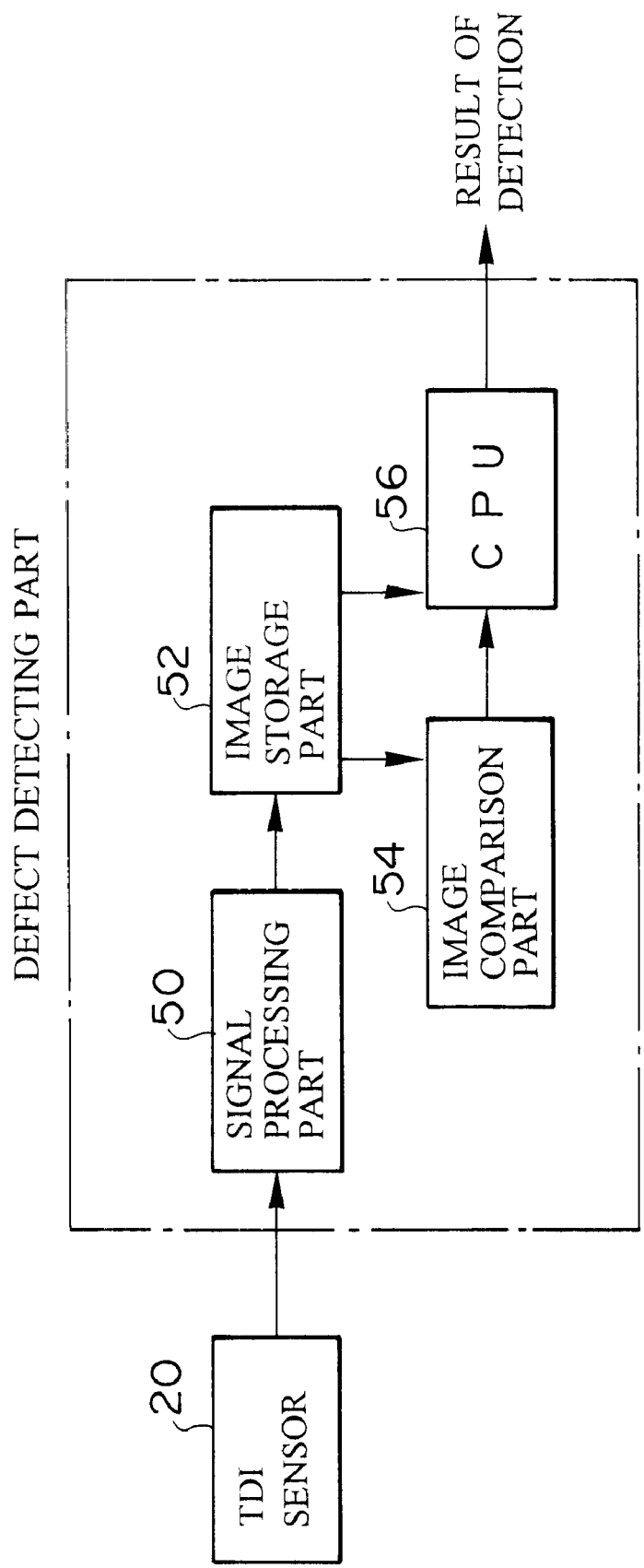
FIG. 3 is a block diagram showing an embodiment of a defect detecting part.

FIG. 3 is a block diagram showing an embodiment of the defect detecting part in the control part 12. As shown in FIG. 3, the defect detecting part comprises a signal processing part 50, an image storage part 52, an image comparison part 54, and a CPU 56.

The signal processing part 50 receives image signals sequentially from the TDI sensor 20, and converts the image signals into digital image data. The signal processing part 50 outputs the image data to the image storage part 52.

The image storage part 52 is composed of a memory such as a RAM. The image data, which is output from the signal processing part 50, is sequentially stored in the image storage part 52.

The image comparison part 54 reads the image data sequentially from the image storage part 52, and compares the image data of a pair of chips that are adjacent to one another along the X-axis to detect the defective part in the chips. The image comparison part 54 sends the results to the CPU 56.

The CPU 56 compares the image data of a possible defective chip determined by the image comparison part 54 with image data of a chip different from the chip with which the possible defective chip has been compared, so as to determine whether the possible defective chip is really defective or not. The CPU 56 finds defective chips in this way and outputs the results to a monitor, etc.

Figure 4:
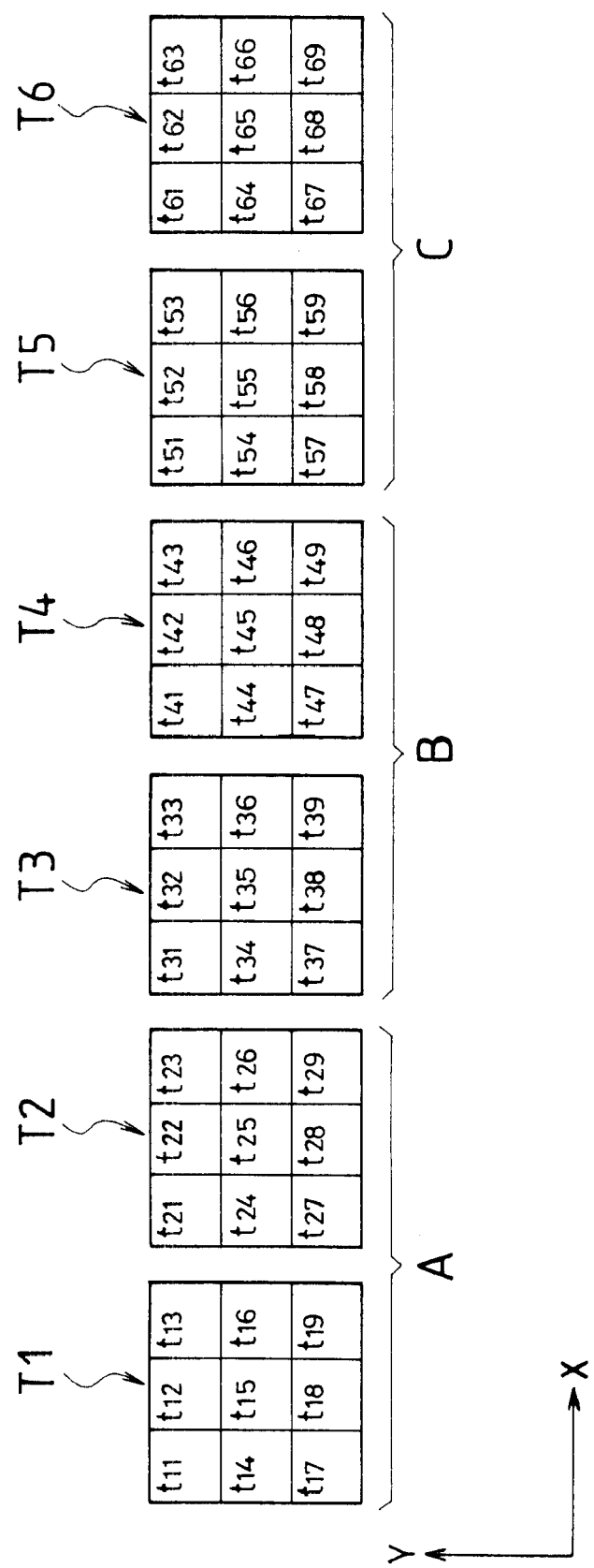
FIG. 4 is an explanation drawing showing the operation of a defect detecting part.
Figure 5:
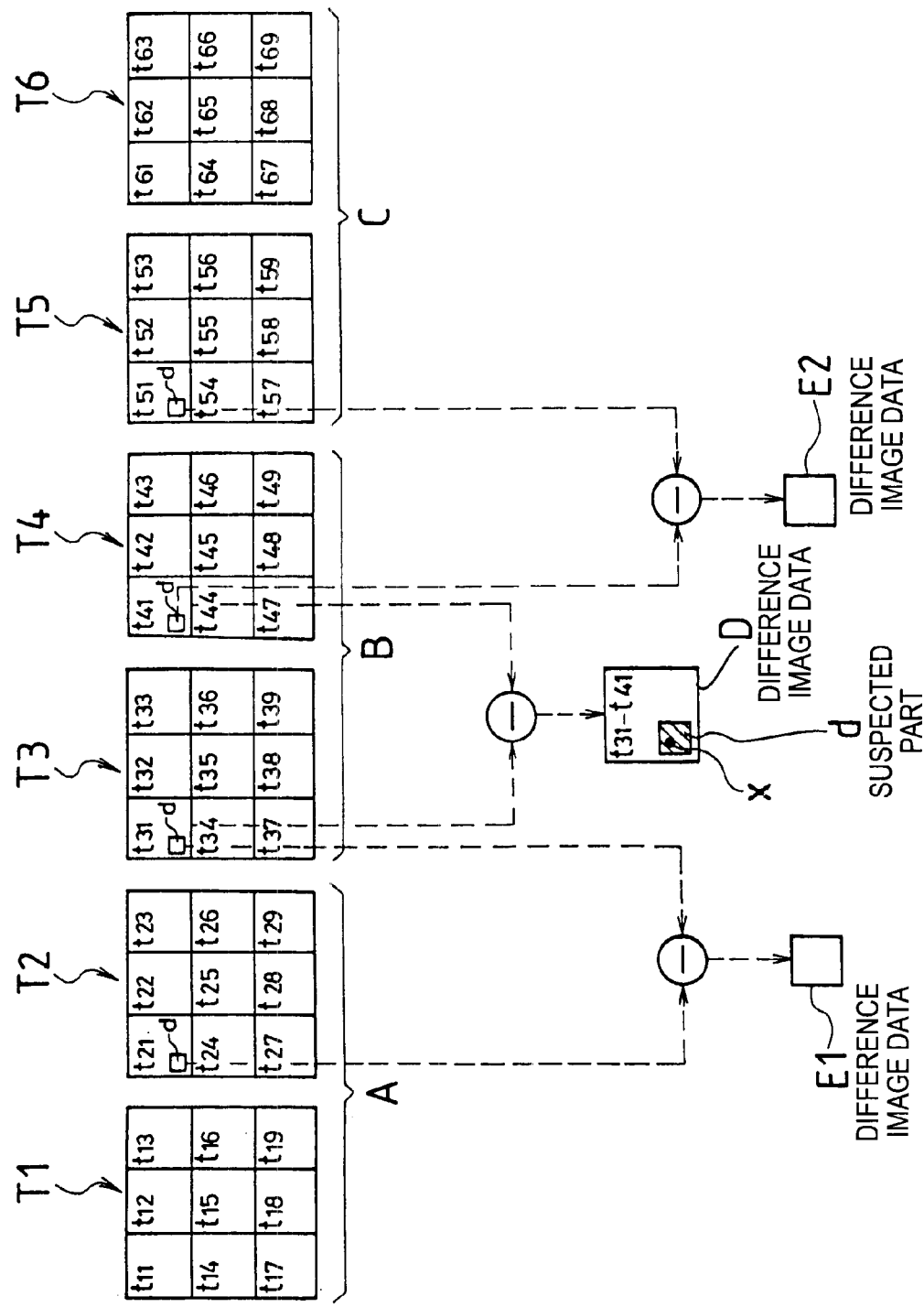
FIG. 5 is an explanation drawing showing the operation of the defect detecting part.

A detailed description will now be given of the operation of the defect detecting part with reference to the explanation drawings of FIGS. 4 and 5. In the case that six chips T1–T6 are arranged along the X-axis (the scanning direction) of the wafer W as shown in FIG. 4, the image data of the chips T1–T6 are divided into image data of a plurality of frames $t_{mn}$ (m= integral number 1–6; n= integral number 1–9) and are recorded sequentially in the image storage part 52. The width of each frame along the Y-axis is the scanning width of the TDI sensor 20, and the width of each frame along the X-axis is predetermined arbitrarily. Although one chip is divided into nine frames (3×3 frames) to simplify the description in FIGS. 4 and 5, the number of divided frames actually varies according to the size of the chip, the scanning width of the TDI sensor 20, etc.

If the scanning starts at a frame $t_{11}$ on the first line of the chip T1 in the case that the TDI sensor 20 scans the wafer W on the scanning track in FIG. 2, the image data of the frames on the first line of the chips T1–T6 are sequentially recorded in the image storage part 52, and the image data of the frames on the second line of the chips T6-T1 are sequentially recorded in the image storage part 52. Then, the image data of the frames on the third line of the chips T1–T6 are sequentially recorded in the image storage part 52.

The image comparison part 54 designates the chips T1–T6 arranged along the X-axis in pairs of two adjacent chips in such a way that one chip does not belong to two pairs or more. For example, the chips T1 and T2 are paired as A; the chips T3 and T4 are paired as B; and the chips T5 and T6 are paired as C. A pair of frames at the same position in the two chips (the frames $t_{mn}$ with the same value of n) in each pair A-C are compared.

As the image data of the frames are sequentially recorded in the image storage part 52, the image comparison part 54 reads the image data of two frames subjected to comparison from the image storage part 52. The image comparison part 54 compares the image data and detects a defective part in those frames. Then, the image comparison part 54 reads the image data of another two frames subjected to the next comparison from the image storage part 52 to perform the same processing.

A description will now be given of the processing performed by the image comparison part 54. As shown in FIG. 5, in the case that the TDI sensor 20 reads the image data of frames $t_{31}$ and $t_{41}$ subjected to comparison in the pair B and the image data is recorded in the image storage part 52 and the image comparison part 54 reads the image data, the image comparison part 54 finds difference between image data of the frames $t_{31}$ and $t_{41}$ with respect to each pixel.

Then, the image comparison part 54 calculates the difference image data D in which value of each pixel is the difference.

If there is no defective part in the frames $t_{31}$ and $t_{41}$, all the pixels of the difference image data D represent smaller values than a predetermined threshold. If there is at least one defective part in at least one of the frames $t_{31}$ and $t_{41}$, a defective pixel corresponding to the defective part represents a larger value than the threshold. The threshold is determined according to the sensitivity for detecting the defective part.

After calculating the difference image data D, the image comparison part 54 compares the value of each pixel in the difference image data D with the threshold. If the values of all the pixels are equal to or less than the threshold, the image comparison part 54 determines that there is no defective part in the frames $t_{31}$ and $t_{41}$. The image comparison part 54 sends the determination results to the CPU 56.

On the other hand, if a larger value than the threshold is detected in any pixel of the difference image data D, the image comparison part 54 determines that there is at least one defective part in the frame $t_{31}$ and/or $t_{41}$ and sends the determination results to the CPU 56. The determination results include the data indicating the position of the defective pixel as well as the data indicating the presence of the defect.

Thereafter, the CPU 56 compares the image data of only the frames in the possible defective pair that have been determined as being possibly defective by the image comparison part 54, with the image data of the frames in another pair. With respect to the frames that have been determined as being not defective, the CPU 56 only receives the results from the image comparison part 54 and does not perform any processing that will be described below for the frames. This reduces the processing time of the CPU 56, and eliminates the necessity of employing a CPU with a high processing capability in the visual inspection apparatus of the present invention.

In the case that the image comparison part 54 detects a defective part χ in the difference image data D, the CPU 56 reads image data of the frame $t_{31}$ in the chip T3 and image data of a frame $t_{21}$ of the chip T2 in the pair A adjacent to the chip T3 from the image storage part 52. At this time, the CPU 56 does not read all the image data of the frames $t_{31}$ and $t_{21}$, but reads only the image data within a predetermined suspected part d including the defective pixel, which has been determined in the difference image data D. Incidentally, all the image data of the frames may be read. The CPU 56 calculates difference image data E1 of the image data of the frames $t_{31}$ and $t_{21}$ within the suspected part d in the same manner as the image comparison part 54, and compares a value of each pixel in the difference image data E1 with the threshold. If a larger value than the threshold is detected, the CPU 56 determines that there is a defective part in the frame $t_{31}$ of the chip T3, and outputs the determination results indicating the presence of the defective part in the chip T3 to the monitor.

On the other hand, if all the values in the difference image data E1 are equal to or less than the threshold, the CPU 56 determines that there is no defective part in the frame $t_{31}$ of the chip T3. Then, the CPU 56 calculates difference image data E2 of the image data of the frames $t_{41}$ of the chip T4 and a frame $t_{51}$ of the chip T5 in the pair C adjacent to the chip T4, and compares a value of each pixel in the difference image data E2 with the threshold. If a larger value than the threshold is detected, the CPU 56 determines that there is a defective part in the frame $t_{41}$ of the chip T4 and outputs the determination results indicating the presence of the defect in the chip T4 to the monitor. If all the values in the difference image data E2 are equal to or less than the threshold, the CPU 56 determines that there is no defective part in the frame $t_{41}$ of the chip T4.

Figure 6:
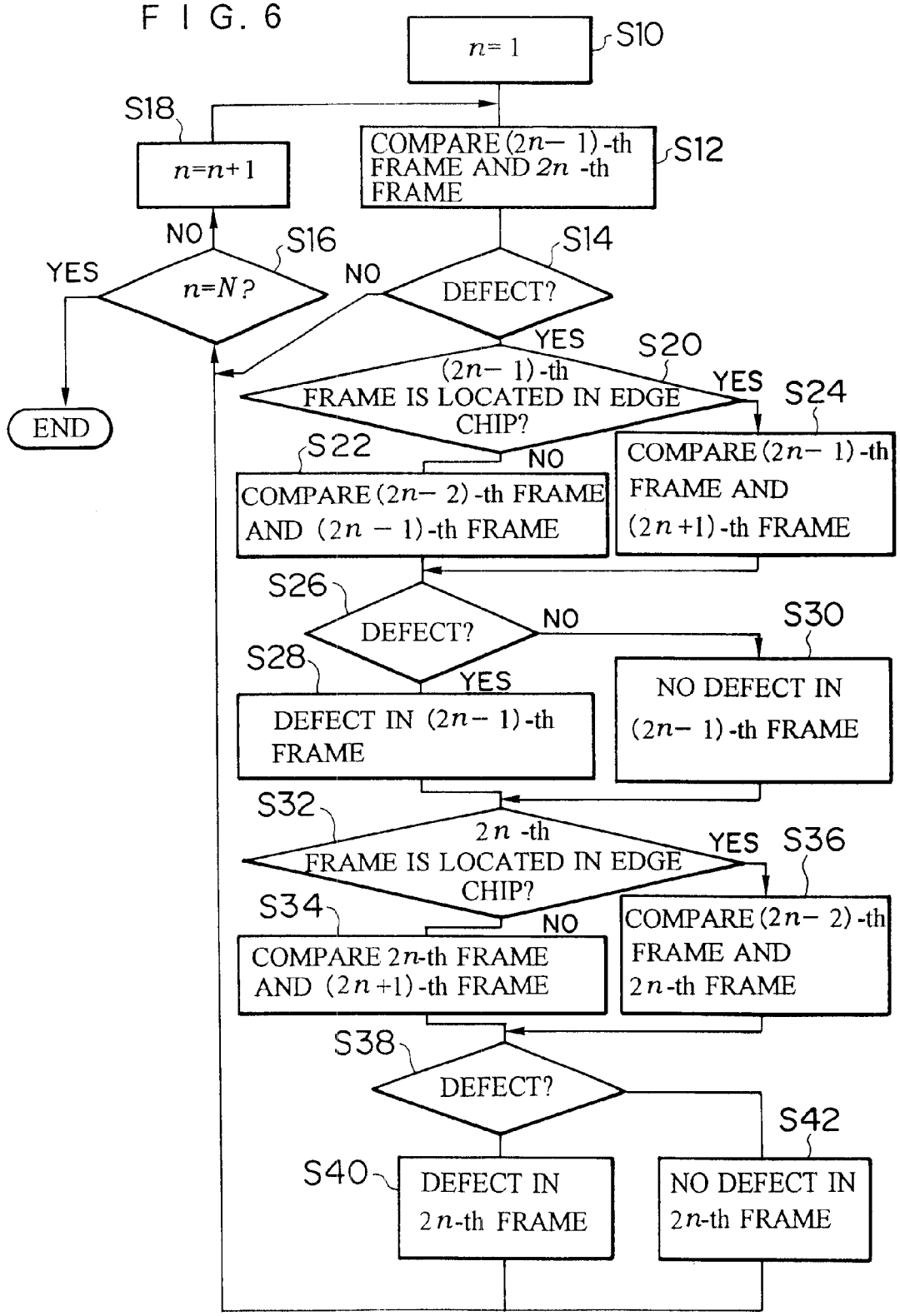
FIG. 6 is a flow chart showing the generalized procedure for comparing image data of frames and detecting a defective part.

FIG. 6 is a flow chart generalizing the procedure of the image comparison part 54 and the CPU 56 for comparing the image data of the frames and detecting defective parts. In FIG. 6, only the frames at corresponding positions in the chips arranged along the X-axis, are explained. The frame at the certain position of an n-th chip from the left is referred to as an n-th frame. The (n−1)-th frame and the (n+1)-th frame are at the same position as the n-th frame in chips adjacent to the chip including the n-th frame. The total number of the chips along the X-axis is 2N (N is an integral number), and the first frame through the 2N-th frame are at the same position of the chips.

At first, the image comparison part 54 sets the variable n as 1 (S10), and reads the image data of the (2n−1)-th frame and the 2n-th frame from the image storage part 52 and compares the image data between these two frames (S12). Specifically, the first frame and the second frame are subjected to the comparison. Then, the image comparison part 54 determines whether there is any defect or not in these frames (S14). If the image comparison part 54 determines that there is no defect, it determines whether the variable n is equal to N or not, specifically whether the 2n-th frame is the last frame or not (S16). If the 2n-th frame is not the last frame, the image comparison part 54 increases the variable n by 1 (S18) and reads the image data of the next two frames subjected to comparison (the third frame and the fourth frame) from the image storage part 52. Then, the image comparison part 54 compares the image data between the third and fourth frames. If no defect is detected from the frames and the variable n is determined as being equal to N at S16, the image comparison part 54 finishes the comparison and determination.

On the other hand, if a defect is detected at S14, the CPU 56 determines whether the (2n−1)-th frame is located in the chip at the left end (S20). In other words, the CPU 56 determines whether (2n−1) is equal to 1 or not. If the (2n−1)-th frame is not located in the chip at the left end, the CPU 56 reads the image data of the (2n−1)-th frame and the adjacent (2n−2)-th frame from the image storage part 52. Then, the CPU 56 compares the image data between the (2n−1)-th frame and the (2n−2)-th frame (S22). The suspected part for reading the image data has already been described.

On the other hand, if the (2n−1)-th frame is located in the chip at the left end (the first frame), the CPU 56 reads the image data of the (2n−1)-th frame and the (2n+1)-th frame (the third frame) from the image storage part 52. The CPU 56 compares the image data between the (2n−1)-th frame and the (2n+1)-th frame (S24).

Then, the CPU 56 determines whether there is any defect in the frames (S26). If there is a defect, the CPU 56 determines that there is a defect in the (2n−1)-th frame (S28) and determines that there is a defect in the chip including the (2n−1)-th frame. On the other hand, if there is no defect, the CPU 56 determines that there is no defect in the (2n−1)-th frame (S30).

Thereafter, the CPU 56 also performs the comparison and determination for the 2n-th frame in the same manner as in the comparison and determination for the (2n−1)-th frame. First, the CPU 56 determines whether the 2n-th frame is located in the chip at the right end (S32). In other words, the CPU 56 determines whether 2n is N or not. If the 2n-th frame is not located in the chip at the right end, the CPU 56 reads the image data of the 2n-th frame and the (2n +1)-th frame adjacent to the 2n-th frame from the image storage part 52 and compare the image data between the 2n-th frame and the (2n+1)-th frame (S34).

On the other hand, if the 2n-th frame is located in the chip at the right end (the 2N-th frame), the CPU 56 reads the image data of the 2n-th frame and the (2n−2)-th frame (the (2N−2)-th frame), which is the second frame to the left from the 2n-th frame, from the image storage part 52. Then, the CPU 56 compares the image data between the 2n-th frame and the (2n−2)-th frame (S36).

Consequently, the CPU 56 determines whether there is any defect or not in the frames (S38). If there is any defect, the CPU 56 determines that there is a defect in the 2n-th frame (S40) and determines that there is a defect in the chip including the 2n-th frame. On the other hand, if there is no defect, the CPU 56 determines that there is no defect in the 2n-th frame (S42).

Thereafter, the CPU 56 determines whether the variable n is equal to N or not (S16). If the variable n is not equal to N, the CPU 56 increases the variable n by 1(S18) and repeats the processing from S12. If the variable n is equal to N at S16, the CPU 56 finishes the comparison and determination. Thus, the determination about the presence of the defect is completed for the frames at the corresponding positions in all the chips arranged along the X-axis.

As set forth hereinabove, the image comparison part 54 does not always perform the comparison and determination twice for all the frames. The image comparison part 54 performs the comparison and determination once for all the frames, and then the CPU 56 performs the comparison and determination only for the suspected frame, which has been determined as being possibly defective by the image comparison part 54. This reduces the processing of the defect detecting part to almost fifty percent of that of the prior art, and increases the processing speed.

In the above-descried example, the total number of the chips arranged along the X-axis is an even number. Thus, no chip is left over when the chips are designated in the pairs as shown in FIG. 4. If, however, the total number of chips is an odd number, one chip is left over. In this case, one of the other chips is duplicatively paired with the leftover chip so that the defect in the leftover chip can be detected in the above-described comparison and determination procedure.

In this embodiment, the image comparison part 54 compares the image data in a pair of adjacent chips, but the adjacent chips are not necessarily paired. Comparing the image data in a pair of separate chips also reduces the processing and increases the processing speed.

The comparison of the image data and the determination about the presence of the defect may be sequentially performed while the TDI sensor 20 is obtaining the image data or after the image data of all the chips are obtained. If the comparison and determination are sequentially performed while the TDI sensor 20 is obtaining the image data, it is possible to use a memory with a small capacity that can store the image data of at least three frames as the image storage part 52. This reduces the cost of the memory.

In this embodiment, the present invention is applied to the visual inspection apparatus for inspecting the wafer on which the chips with the same pattern are arranged, but the present invention may also be applied to a visual inspection apparatus for inspecting an arbitrary object other than the wafer.

As set forth hereinabove, according to the visual inspection apparatus of the present invention, the images in all areas on the object are not always compared twice. Two areas are paired and the images are compared in each pair. Only the images in the suspected pair having a possibility of being defect are compared with images in other pairs. This reduces the number of comparisons to almost fifty percent of the prior art and increases the processing speed while maintaining the reliability of the conventional double detection.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. A visual inspection apparatus, comprising:

imaging means for obtaining images of a plurality of areas on an object;

first image comparison means for designating the plurality of areas in pairs and comparing the images of the areas in each of the pairs to determine whether said each of the pairs is a defective pair including a defective area containing a defective part; and second image comparison means for comparing the image of one of the areas in the pair determined as the defective pair by the first image comparison means with the image of one of the areas in another of the pairs to determine whether the one of the areas in the pair determined as the defective pair is the defective area.

2. The visual inspection apparatus as defined in claim 1, wherein the first image comparison means designates the plurality of areas in the pairs of two areas adjacent to one another.

3. The visual inspection apparatus as defined in claim 2, wherein the second image comparison means compares the image of the one of the areas in the pair determined as the defective pair with the image of one of the areas in another of the pairs adjacent to the one of the areas in the pair determined as the defective pair.

4. The visual inspection apparatus as defined in claim 1, wherein the second image comparison means compares only a suspected part, including a possible defective part determined by the first image comparison means, of the image of the one of the areas in the pair determined as the defective pair with a part, corresponding to the suspected part, of the image of the one of the areas in said another of the pairs.

5. A visual inspection method, comprising the steps of:

obtaining images of a plurality of areas on an object;

designating the plurality of areas in pairs;

comparing the images of the areas in each of the pairs to determine whether said each of the pairs is a defective pair including a defective area containing a defective part; and comparing the image of one of the areas in the pair determined as the defective pair in the former comparing step with the image of one of the areas in another of the pairs to determine whether the one of the areas in the pair determined as the defective pair is the defective area.

6. The visual inspection method as defined in claim 5, wherein, in the designating step, the plurality of areas are designated in the pairs of two areas adjacent to one another.

7. The visual inspection method as defined in claim 6, wherein, in the latter comparing step, the image of the one of the areas in the pair determined as the defective pair is compared with the image of one of the areas in another of the pairs adjacent to the one of the areas in the pair determined as the defective pair.

8. The visual inspection method as defined in claim 5, wherein, in the latter comparing step, only a suspected part, including a possible defective part determined in the former comparing step, of the image of the one of the areas in the pair determined as the defective pair is compared with a part, corresponding to the suspected part, of the image of the one of the areas in said another of the pairs.

\* \* \* \* \*